United States Patent [19]
Ichiki et al.

[11] Patent Number: 5,210,229
[45] Date of Patent: May 11, 1993

[54] PROCESS FOR THE PREPARATION OF GAMMA-BUTYROLACTONE

[75] Inventors: Tatsumi Ichiki; Kaori Mori; Sadakatsu Suzuki; Hiroshi Ueno; Kenji Kobayashi, all of Saitama, Japan

[73] Assignee: Tonen Chemical Corporation, Tokyo, Japan

[21] Appl. No.: 915,076

[22] Filed: Jul. 16, 1992

[30] Foreign Application Priority Data

Jul. 17, 1991 [JP] Japan .................................. 3-201066
Nov. 20, 1991 [JP] Japan .................................. 3-329752
Apr. 8, 1992 [JP] Japan .................................. 4-114257

[51] Int. Cl.$^5$ .......................................... C07D 307/28
[52] U.S. Cl. ..................................................... 549/295
[58] Field of Search ........................................ 549/295

[56] References Cited

U.S. PATENT DOCUMENTS

| | | | |
|---|---|---|---|
| 3,374,184 | 3/1968 | McEvoy et al. | 549/503 |
| 4,356,310 | 10/1982 | Brima | 549/295 |
| 5,110,954 | 5/1992 | Bellis | 549/295 |

FOREIGN PATENT DOCUMENTS

| | | |
|---|---|---|
| 0301853 | 2/1989 | European Pat. Off. |
| 0013573 | 1/1983 | Japan |
| 0468918 | 4/1975 | U.S.S.R. |
| 0745903 | 7/1980 | U.S.S.R. |

*Primary Examiner*—C. Warren Ivy
*Assistant Examiner*—A. A. Owens
*Attorney, Agent, or Firm*—Kane, Dalsimer, Sullivan, Kurucz, Levy, Eisele and Richard

[57] ABSTRACT

Gamma-butyrolactone is prepared by catalytic dehydrogenation of 1,4-butanediol in a gaseous phase in the presence of a catalyst comprising copper, chromium, and manganese and/or barium. Improvement is in that the catalyst further contains sodium and/or potassium, whereby formation of by-products is suppressed and high yield, high selectivity and prolonged catalyst life are attained.

14 Claims, 2 Drawing Sheets a: Cu-Cr-Mn
b: Cu-Cr-Mn-Na

PROCESS FOR THE PREPARATION OF GAMMA-BUTYROLACTONE

FIELD OF THE INVENTION

The present invention relates to a process for the preparation of γ-butyrolactone, more specifically, by catalytic dehydrogenation of 1,4-butanediol in a gaseous phase in the presence of catalyst.

PRIOR ART

γ-Butyrolactone is a useful compound as a solvent or an intermediate product for the preparation of pyrrolidones such as N-methyl pyrrolidone. Accordingly, there is an eager need for a less costly and efficient process for the preparation of γ-butyrolactone.

Known processes for the preparation of γ-butyrolactone include (1) a method where 1,4-butanediol is subjected to oxidative dehydrogenation in the presence of catalyst such as palladium, platinum or silver, (2) a method where maleic anhydride or ester thereof is catalytically hydrogenated in the presence of catalyst, and (3) a method where 1,4-butanediol is dehydrogenated in the presence of Cu-Cr type catalyst.

However, the method (1) has drawbacks that the catalyst is less active and selectivity for γ-butyrolactone is low. The method (2) has a disadvantage that the life of catalyst is short both in liquid phase reaction and in gaseous phase reaction. The method (3) is now generally used, but has drawbacks that noticeable amounts of by-products such as tetrahydrofuran and butanol arise, so that yield and selectivity for γ-butyrolactone are not always good. It was proposed to add manganese or zinc to the Cu-Cr catalyst (Japanese Patent Application Laid-Open No. Sho-61-246173/86), which is however unsatisfactory. The present inventors proposed to add manganese and barium to the Cu-Cr catalyst in Japanese Patent Application Laid-Open No. Hei-3-232,875 which was published on Oct. 16, 1991. This is not always satisfactory. The method (3) further has another problem that the life of catalyst is not satisfactory. In the above JP Application Laid-Open No. Sho-61-246173/86, it is stated that the life of catalyst is improved by the addition of manganese or zinc. However, the life was prolonged for only 1 month at most in the Examples, which is not satisfactory in a commercial aspect. Further, a manner is known where a reaction temperature is raised with the decreasing activity in order to sustain the activity, which is called temperature increased run or TIR for short. However, the selectivity for γ-butyrolactone at high temperatures is not high in the previous catalyst systems and, accordingly, the elevation of the reaction temperature does not always lead to sustenance of the activity.

In general, the Cu-Cr type catalyst is activated by reduction with hydrogen in advance of the reaction. For instance, the reduction is carried out at 180° to 200° C. or 200° to 210° C. in a hydrogen flow in JP Application Laid-Open Sho-61-246173/86. In a usually recommended reduction method, catalyst is heated up to a reduction temperature of 150° to 160° C. in a nitrogen atmosphere, then hydrogen is added to nitrogen so as to gradually increase a hydrogen concentration while raising the reduction temperature. When no rise in temperature due to reduction reaction is observed any more at a reduction temperature of 200° C. and a hydrogen concentration of 100%, the reduction procedure is ended. In a reduction method with temperature rise, called temperature programmed reduction or TPR, where catalyst is reduced in the presence of hydrogen at a constant speed of temperature rise and consumption of the hydrogen is observed, a temperature of the start of reduction determined for the Cu-Cr type catalyst shows that no consumption of hydrogen occurs below 140° C.

SUMMARY OF THE INVENTION

The purpose of the invention is to provide a process for the preparation of γ-butyrolactone in which formation of by-products is prevented and high yield and high selectivity are attained.

The present inventors have made research about various processes for the preparation of γ-butyrolactone by catalytic dehydrogenation of 1,4-butanediol in a gas phase and have found that a Cu-Cr type catalyst which further contains manganese and/or barium, and sodium and/or potassium may be used for the preparation of γ-butyrolactone, prevents formation of by-products and gives high yield and high selectivity, and further has the life of catalyst which is greatly improved.

Thus, the prevent invention is a process for the preparation of γ-butyrolactone by catalytic dehydrogenation of 1,4-butanediol in a gaseous phase in the presence of a catalyst which contains copper, chromium, and at least one member selected from the group consisting of manganese and barium, characterized in that the catalyst further contains at least one member selected from the group consisting of sodium and potassium.

It has also been found that the Cu-Cr catalyst which further contains at least one member selected from the group consisting of manganese and barium, and at least one member selected from the group consisting of sodium and potassium is made more active by a reduction method where the catalyst is placed in a gas flow containing a small amount of hydrogen at a temperature below 40° C. and preheated to a temperature of from 100° to 140° C. and then the temperature and the hydrogen concentration are raised.

Thus, in a preferred embodiment of the invention, the catalyst is subjected to reduction treatment in which the catalyst is preheated from a temperature below 40° C. to a temperature of from 100° to 140° C. in a flow of an inert gas containing 0.1 to 1% by volume of hydrogen and then the temperature and the hydrogen concentration are gradually raised.

DESCRIPTION OF THE PREFERRED EMBODIMENT

Figure 1:
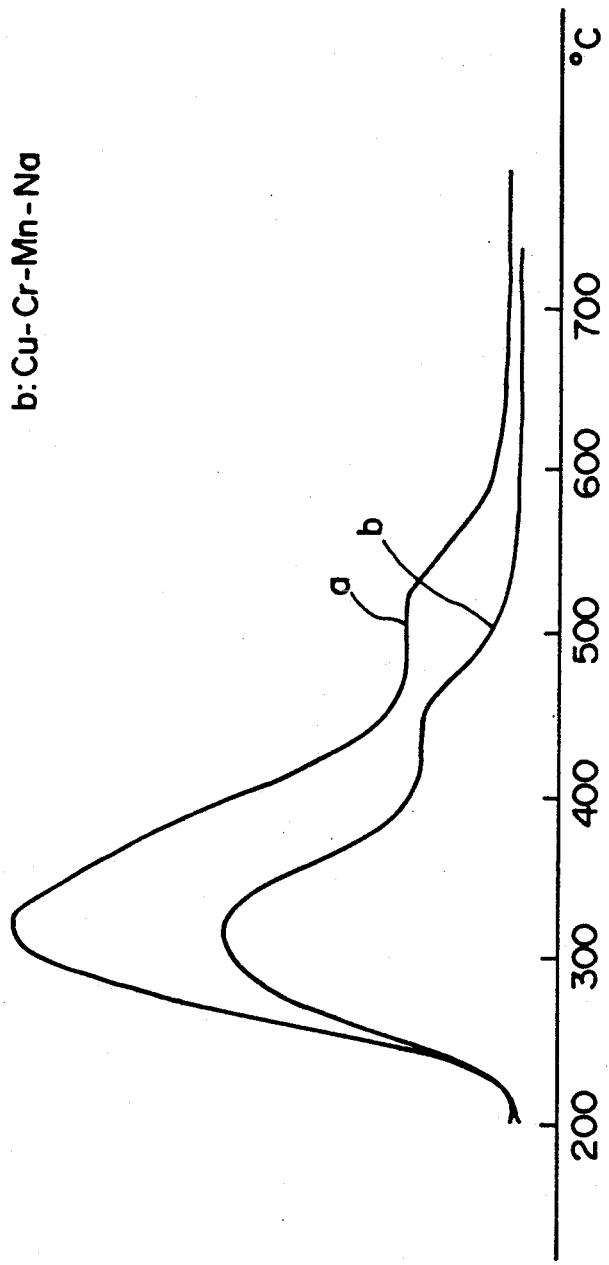
FIG. 1 shows temperature programmed desorption (TPD) profiles of pyridine on catalysts where curve (a) corresponds to the Cu-Cr-Mn catalyst prepared in Comparison Example 1 and curve (b) corresponds to the Cu-Cr-Mn-Na catalyst prepared in Example 1.

The catalyst used in the process of the invention contains manganese and/or barium, and sodium and/or potassium in addition to copper and chromium. The other alkali metals (e.g., lithium, rubidium and cesium) than sodium and potassium are not suitable for use. An atomic ratio of copper to chromium is preferably 0.4 to 1.8, more preferably 0.8 to 1.4. Manganese is contained preferably in an amount of 1 to 10 parts by weight, more preferably 2 to 7 parts by weight, per 100 parts by weight of the total of copper and chromium. Barium is contained preferably in an amount of 2 to 20 parts by weight, more preferably 2 to 10 parts by weight, per 100 parts by weight of the total of copper and chromium. When both manganese and barium are contained, their total is preferably 3 to 30 parts by weight per 100 parts by weight of the total of copper and chromium. Sodium and potassium is contained preferably in an amount of 0.1 to 10 parts by weight, more preferably 0.5 to 7 parts by weight, as alkali metals per 100 parts by weight of the total of copper and chromium. In addition, a small amount of silicon may be contained up to 10 parts by weight per 100 parts by weight of the total of copper and chromium.

The above catalyst may be prepared as follows: copper nitrate, copper sulfate, copper chloride or copper acetate may be used as a copper source; dichromate (e.g., $Na_2Cr_2O_7$), chromate or chromium nitrate as a chromium source; barium chloride, barium nitrate, manganese chloride, manganese nitrate and manganese acetate as a manganese or barium source; and carbonate, silicate (water glass) or hydroxide as a sodium or potassium source. A chromium-containing solution is made basic by ammonium and admixed with a solution containing copper, and manganese and/or barium to form precipitates.

The precipitates thus obtained are filtrated, washed with water, dried, and then pyrolyzed at 300° to 400° C. The powder obtained is washed with an aqueous dilute acid solution, washed with water and dried. To the catalyst precursor obtained is added a compound containing sodium and/or potassium, dried and calcined at 400° to 500° C. Timing of the addition of sodium and/or potassium is not particularly limited, but these alkali metals are highly water-soluble and, therefore, are usually added after the aforesaid precipitates formed are washed with water and dried, or after the subsequent calcination. Then, molding auxilliaries such as graphite may be added if needed, and a predetermined shape is formed using a molding machine. Each component exists in the form of oxide in the resultant catalyst.

Reduction of the catalyst may be carried out for instance as follows: nitrogen gas which generally contains about 3% by volume of hydrogen is passed to the catalyst at a gas hourly space velocity (G.H.S.V.), reduced at normal temperature and pressure, of 4000 to 8000 $hr^{-1}$ (hereinafter, G.H.S.V. is always a value reduced at normal temperature and pressure), under pressure of several kilograms per $cm^2$ in gauge, heated at 140° to 160° C. until heat generation is not observed any more in the catalyst bed; then the hydrogen concentration and the temperature are gradually raised, and hydrogen of 100% by volume is passed at a catalyst bed temperature of 200° C. for several hours.

In a preferred embodiment, the catalyst is subjected to the following reduction treatment. That is, (1) while an inert gas which contains 0.1 to 1% by volume of hydrogen is passed as a reducing gas, the catalyst is preheated from a temperature below 40° C. to a temperature of from 100° to 140° C. (pre-reduction temperature), and then (2) the temperature and the hydrogen concentration are gradually raised. It is known from JP Application Laid-Open No. Hei-1-127042/89 that such reduction treatment enhances activity of copper-chromium catalyst in the preparation of 1,4-butanediol by hydrogenation of maleic diester. It has now been found that this treatment also has an effect of increasing activity of the Cu-Cr-Mn and/or Ba-Na and/or K catalyst in the preparation of $\gamma$-butyrolactone by dehydrogenation of 1,4-butanediol according to the invention.

First, step (1) will be explained below. Step (1) is a pre-heating step. The hydrogen concentration of a reducing gas is 0.1 to 1% by volume, preferably 0.1 to 0.5% by volume. If the hydrogen concentration is lower than the above range, the reduction rate is so slow that the reduction treatment takes too much time. If it exceeds the above range, temperature rise during the reduction is too large. Examples of the inert gas include nitrogen, helium, neon, argon, xenon, methane, ethane and butane. These may be used alone or as a gas mixture of two or more of these. Nitrogen gas is preferred. More preferably, the gas is substantially free of oxygen. In typical conditions, a gas flow rate corresponds generally to a gas hourly space velocity (G.H.S.V.) of about 400 to 6000 $hr^{-1}$, preferably about 1000 to 3000 $hr^{-1}$, reduced at normal temperature and pressure. It is preferred that during this step the catalyst is heated always in an inert gas flow containing 0.1 to 1% by volume of hydrogen from a temperature below 40° C., preferably from room temperature, to a pre-reduction temperature. However, it is also allowed to start heating in an inert gas and, at a proper temperature (e.g., about 40° C.), to introduce a hydrogen-containing inert gas. When a temperature in this step is closer to the aforesaid pre-reduction temperature, it becomes more critical that the catalyst is in contact with hydrogen gas (i.e., reducing gas). The preheating in step (1) may be started from a lower temperature, e.g., 0° C., but almost no additional benefit is obtained. Step (1) may be conducted at normal or reduced pressure, but is carried out preferably under pressure of about 1 to 20 $kg/cm^2G$, more preferably about 2 to 10 $kg/cm^2G$. The heating takes preferably about 30 minutes to 6 hours from a temperature below 40° C. to a pre-reduction temperature. It is preferred that the temperature rises substantially linearly during this step, where a speed of temperature rise is preferably 5° to 40° C. per hour. It is also possible to raise the temperature stepwise with a temperature step of about 5° to 10° C., and maintain the temperature constant for a certain period of time.

Next, the step (2) will be explained below. The temperature and the hydrogen concentration are gradually increased in this step. In a preferred embodiment of this step, the temperature is increased gradually up to a reduction temperature such as 150° to 200° C. and, while maintaining this reduction temperature or further increasing the temperature, the hydrogen concentration in a reducing gas is gradually increased up to the final hydrogen concentration of 100% by volume, and thereafter the temperature is raised finally up to 180° to 250° C. Procedure followed after the reduction temperature is reached may be the same as reduction treatment conventional for Cu-Cr catalyst.

In the whole period, catalyst may be heated according to a temperature vs time profile, i.e., heating speed, which makes it possible to maintain the catalyst in reduction conditions where the gas composition in the gas inlet and that in the gas outlet are as similar with each other as possible. It is preferred to raise the temperature linearly up to the reduction temperature, e.g., 150° to 200° C. The rate of temperature rise is preferably about 1° to 15° C. per hour, more preferably about 10° C. per hour. It is also possible to raise the temperature stepwise. For instance, the temperature may be raised stepwise by about 5° to 10° C. and held constant for a certain period. After, during and before heating at each step, it is carefully observed that the gas composition at the gas inlet is similar with that at the gas outlet.

After the temperature of catalyst reaches a reduction temperature, it is preferred that while maintaining the temperature around the reduction temperature or rising it, the hydrogen concentration is increased gradually. However, it should be strictly observed that the gas composition at the gas inlet is substantially the same as that at the gas outlet during whole of this period of catalyst activation. It is preferred to raise the hydrogen concentration first stepwise by about 0.05 to 0.3% by volume at a slow pace, then by 1 to 10% by volume up to the final hydrogen percent by volume of 100. Preferably, after the hydrogen concentration reaches 100% by volume, the reduction temperature is raised to the final temperature, i.e., 180° to 250° C., and reduction treatment is ended.

In this embodiment, temperature difference between a catalyst bed and a heating apparatus, $\Delta T$, due to heat generation of a catalyst bed is suppressed to be preferably at most 5° C. during the whole reduction treatment.

A gas mixture comprising 1,4-butanediol and hydrogen may be contacted with the catalyst in any manner which may be properly selected among conventional ones, for instance, in a fixed bed, in a moving bed or in a fluidized bed. Alternatively, the gas mixture may be contacted with the catalyst batchwise.

The reaction according to the invention is equilibrium reaction represented by the following scheme:

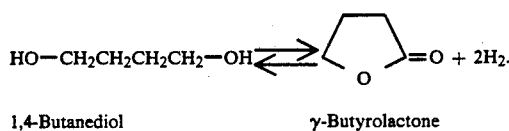

1,4-Butanediol    γ-Butyrolactone

The above equilibrium shifts toward the formation of γ-butyrolactone with a higher temperature, lower pressure and lower volume ratio of hydrogen to 1,4-butanediol. If the reaction temperature is too high, the life of catalyst becomes shorter due to formation of cokes and sintering of copper metal particles, and the selectivity for γ-butyrolactone decreases due to side reactions. However, the process of the invention can prevent side reactions and, therefore, higher temperature than previous can be adopted for the reaction. The reaction temperature is preferably 150° to 300° C., more preferably 190° to 270° C. Lower reaction pressure is favourable to the formation of γ-butyrolactone. However, in a range where the equilibrium is on the side of γ-butyrolactone, the rate of formation of γ-butyrolactone is faster under pressure, so that higher yield for γ-butyrolactone is attained. Accordingly, the reaction according to the invention is conducted preferably under pressure such as several kilograms per square centimeter in gauge. More specifically the reaction pressure is preferably 0 to 8 kg/cm²G, more preferably 0.5 to 4 kg/cm²G. A lower ratio of hydrogen to 1,4-butanediol is favourable to the formation of γ-butyrolactone. However, the reaction according to the invention is conducted preferably in a moderate ratio of hydrogen to 1,4-butanediol because the life of catalyst becomes shorter if hydrogen does not exist in the reaction system, and also because a diluent is needed to maintain the system in a gaseous state. Specifically, a mole ratio of hydrogen to 1,4-butanediol is preferably at least a value at which the system is maintained gaseous, i.e., 0.5 to 10, more preferably 2 to 6. A weight hourly space velocity (W.H.S.V.) of 1,4-butanediol is preferably 0.2 to 16 hour$^{-1}$, more preferably 0.4 to 6.0 hour$^{-1}$.

If the reaction temperature is too high in the aforesaid equilibrium reaction (I), a side reaction represented by the following scheme may proceed easily, so that selectivity for γ-butyrolactone becomes worse:

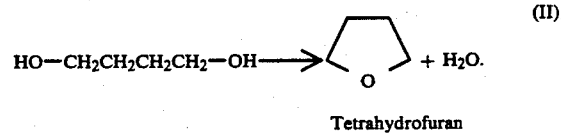

Tetrahydrofuran

This side reaction is dehydration reaction and it is believed that acidic points present on the Cu-Cr catalyst catalyze the side reaction. The acidic points further cause formation of heavier materials and coking, and accelerate deterioration of the catalyst. In the present invention on the other hand, the catalyst contains a basic alkali metal, sodium or potassium, which is believed to be a reason why only the side reaction, i.e., dehydration reaction (II), can be prevented while maintaining the activity for dehydrogenation reaction (I); therefore, when the reaction is conducted at a high temperature, conversion of 1,4-butanediol is raised without deterioration of selectivity for γ-butyrolactone, so that γ-butyrolactone can be obtained at high yield: and, further, formation of heavier materials and coking are prevented, so that large improvement on catalyst life is attained. However, the effects of the invention can not be attained with Cu-Cr catalysts which contain other alkali metals than sodium and potassium. It is believed that this is because lithium is too weakly basic to regulate acidic properties of Cu-Cr catalysts; rubidium and cesium are so strongly basic as to remarkably decrease activity for the envisaged dehydrogenation reaction though the formation of a by-product, tetrahydrofuran, is successfully prevented. The effects attained by the addition of sodium or potassium will be clearly seen also from the results of the temperature programmed desorption of pyridine (TPD) described after Example 12 below.

In the process of the invention, it is possible to maintain the activity without damaging the selectivity for γ-butyrolactone even when the reaction temperature is raised, as stated above. This feature is suitable to temperature increased run or TIR. The catalyst used has a long catalyst life, which may further be greatly prolonged by TIR.

The invention will be further explained hereinafter in reference to the following Examples, which however do not restrict the invention.

Comparison Example 1

To a solution of 178.7 g of Na$_2$Cr$_2$O$_7$.2H$_2$O in 900 ml of distilled water were added 225 ml of an aqueous 28% ammonia, which is hereinafter referred to as Solution A.

In 900 ml of distilled water were dissolved 260.4 g of Cu(NO$_3$)$_2$.3H$_2$O and 17.5 g of Mn(NO$_3$)$_2$.6H$_2$O, and heated to 80° C. This solution is hereinafter referred to as Solution B.

Solution B was added to Solution A under stirring. The resultant precipitates were filtered, washed with water, dried and pulverized, which was then pyrolyzed at 350° C. The powder obtained was washed with an aqueous 10% solution of acetic acid, washed with water and dried to obtain a catalyst precursor. The catalyst precursor was calcined at 450° C. for 3 hours, to which graphite was then added in an amount of 0.5% by weight. This was molded into pellets. The composition of the catalyst obtained in an oxide form which was determined in fluorescence X-ray analysis was as follows: 34.3% by weight of Cu, 29.3% by weight of Cr and 4.1% by weight of Mn.

Two and a half (2.5) grams of the catalyst in an oxide form was packed in a stainless steel (SUS 316) fixed bed reactor with a diameter of 15 mm and a length of 600 mm, which was then pressurized to 5 kg/cm$^2$G by a flow of nitrogen, followed by heating up to 120° C. Hydrogen was then added in an amount of 3% by volume to the nitrogen to begin reduction of the catalyst. A total gas flow rate at that time (gas hourly space velocity) was 7200 hr$^{-1}$. The temperature was elevated gradually to 150° C. while confirming that the temperature of the catalyst bed became almost the same as that of the heating apparatus. The concentration of hydrogen was then increased gradually to 30% by volume further while confirming that the temperature of the catalyst bed became almost the same as that of the heating apparatus. The temperature and the hydrogen concentration were alternatively elevated gradually up to a final temperature of 200° C. and a final concentration of hydrogen of 100% by volume. Then, after confirmed that the temperature of the catalyst bed became almost the same as that of the heating apparatus, the reduction was ended. The catalyst was used in the following reaction.

The reactor was heated to 230° C. Then, 1,4-butanediol and hydrogen were passed in a ratio of 1 mole of 1,4-butanediol per 4 moles of hydrogen, at a pressure of 4 kg/cm$^2$G and a weight hourly space velocity of 1,4-butanediol of 3.0 hr$^{-1}$ to conduct dehydrogenation reaction. The products were analyzed in gas chromatography to obtain the following results in mole percent:

| | |
|---|---|
| conversion of 1,4-butanediol | 99.25% |
| selectivity for γ-butyrolactone | 97.14% |
| selectivity for tetrahydrofuran | 1.90%. |

Example 1

To 10 g of the catalyst precursor before calcined in Comparison Example 1 was added 0.6 g of Na$_2$CO$_3$ dissolved in a small amount of water, which was dried and then calcined at 450° C. for three hours. Graphite was added to this in an amount of 0.5% by weight, which was molded into pellets. The composition of the obtained catalyst of an oxide form, which was determined in fluorescence X-ray analysis, was as follows: 33.5% by weight of Cu, 28.6% by weight of Cr, 4.0% by weight of Mn and 2.2% by weight of Na.

The catalyst of an oxide form was reduced as described in Comparison Example 1, and used in dehydrogenation of 1,4-butanediol as described in Comparison Example 1, except that the reaction temperature was 230° C. or 270° C. The results of gas chromatography for each product are as follows in mole percent:

| | 230° C. | 270° C. |
|---|---|---|
| conversion of 1,4-butanediol | 91.39% | 99.49% |
| selectivity for γ-butyrolactone | 98.98% | 97.93% |
| selectivity for tetrahydrofuran | 0.14% | 0.17% |

Comparison Example 2

A catalyst in an oxide form was prepared and molded as described in Comparison Example 1, except that a solution of 260.4 g of Cu(NO$_3$)$_2$.3H$_2$O, 17.5 g of Mn(NO$_3$)$_2$.6H$_2$O and 15.8 g of Ba(NO$_3$)$_2$ dissolved in 900 ml of distilled water was used in place of Solution B in Comparison Example 1. The composition of the catalyst is as shown in Table 1.

After reduction of the catalyst of an oxide form as described in Comparison Example 1, it was used in dehydrogenation of 1,4-butanediol as described in Comparison Example 1, except that the weight hourly space velocity of 1,4-butanediol was 3 hr$^{-1}$ or 9 hr$^{-1}$. The results of each case are as shown in Table 1.

EXAMPLE 2

A catalyst in an oxide form was prepared and molded as described in Comparison Example 2, except that 0.6 g of Na$_2$CO$_3$ dissolved in a small amount of water was added to 10 g of the catalyst precursor before calcination at 450° C. The composition of the catalyst is as shown in Table 1.

After reduction of the catalyst of an oxide form as described in Comparison Example 1, it was used in dehydrogenation of 1,4-butanediol as described in Comparison Example 1, except that the reaction temperature was 230° C. or 270° C. The results of each case are as shown in Table 1.

EXAMPLE 3

A catalyst in an oxide form was prepared as described in Example 2, except that 2.6 g of sodium silicate (water glass No. 1) was used in place of Na$_2$CO$_3$. The composition of the catalyst is as shown in Table 1.

After reduction of the catalyst of an oxide form as described in Comparison Example 1, it was used in dehydrogenation of 1,4-butanediol as described in Comparison Example 1, except that the reaction temperature was 230° C. or 270° C. The results of each case are as shown in Table 1.

EXAMPLE 4

A catalyst in an oxide form was prepared as described in Example 2, except that 4.0 g of potassium silicate (water glass No. 4) was used in place of Na$_2$CO$_3$. The composition of the catalyst is as shown in Table 1.

After reduction of the catalyst of an oxide form as described in Comparison Example 1, it was used in dehydrogenation of 1,4-butanediol as described in Comparison Example 1, except that the weight hourly space velocity of 1,4-butanediol was 3 hr$^{-1}$ or 9 hr$^{-1}$. The results of each case are as shown in Table 1.

Comparison Example 3

A catalyst in an oxide form was prepared and molded as described in Comparison Example 1, except that a solution of 260.4 g of Cu(NO$_3$)$_2$.3H$_2$O and 21.5 g of Ba(NO$_3$)$_2$ dissolved in 900 ml of distilled water was used in place of Solution B in Comparison Example 1. The composition of the catalyst is as shown in Table 1.

After reduction of the catalyst of an oxide form as described in Comparison Example 1, it was used in dehydrogenation of 1,4-butanediol as described in Comparison Example 1, except that the weight hourly space velocity of 1,4-butanediol was 3 hr$^{-1}$ or 9 hr$^{-1}$. The results of each case are as shown in Table 1.

EXAMPLE 5

A catalyst in an oxide form was prepared and molded as described in Comparison Example 3, except that 0.6 g of Na$_2$CO$_3$ dissolved in a small amount of water was added to 10 g of the catalyst precursor before calcination at 450° C. The composition of the catalyst is as shown in Table 1.

After reduction of the catalyst of an oxide form as described in Comparison Example 1, it was used in dehydrogenation of 1,4-butanediol as described in Comparison Example 1, except that the reaction temperature was 230° C. or 270° C. The results of each case are as shown in Table 1.

Comparison Example 4

A catalyst of the same composition as that in Example 6 was prepared except that Na was not contained. Dehydrogenation of 1,4-butanediol was conducted in the same conditions as in Example 6. The results are as shown in Table 3.

TABLE 3

| Reaction Time (hr) | Conversion of 1,4-butanediol (%) | Yield of γ-butyrolactone (%) |
| --- | --- | --- |
| 22 | 99.9 | 97.2 |
| 98 | 99.9 | 97.2 |
| 152 | 99.8 | 97.1 |
| 192 | 99.6 | 96.9 |
| 312 | 99.3 | 96.7 |
| 502 | 98.4 | 95.6 |
| 1007 | 96.5 | 94.1 |
| 1510 | 95.7 | 93.0 |
| 2014 | 91.0 | 88.0 |

TABLE 1

| | Composition of catalyst in an oxide form (wt. %) | | | | | Reaction conditions | | Result (wt. %) | | |
| --- | --- | --- | --- | --- | --- | --- | --- | --- | --- | --- |
| | Cu | Cr | Mn | Ba | alkaline metal | Temp. (°C.) | W.H.S.V. (hr$^{-1}$) | Conversion of BDO | Selectivity for GBL | Selectivity for THF |
| Comp. Ex. 2 | 28.3 | 30.4 | 2.0 | 4.5 | — | 230 | 3 | 99.29 | 97.30 | 1.45 |
| | | | | | | 230 | 9 | 93.70 | 98.22 | 0.68 |
| Example 2 | 27.7 | 29.7 | 2.0 | 4.4 | 2.1(Na) | 230 | 3 | 88.18 | 98.70 | 0.09 |
| | | | | | | 270 | 3 | 97.96 | 97.28 | 0.10 |
| Example 3 | 26.7 | 28.7 | 1.9 | 4.2 | 2.6(Na) | 230 | 3 | 84.51 | 98.30 | 0.19 |
| | | | | | | 270 | 3 | 91.58 | 96.77 | 0.12 |
| Example 4 | 26.6 | 28.6 | 1.9 | 4.2 | 2.3(K) | 230 | 3 | 97.61 | 98.73 | 0.18 |
| | | | | | | 230 | 9 | 81.28 | 98.59 | 0.15 |
| Comp. Ex. 3 | 34.2 | 31.4 | — | 6.0 | — | 230 | 3 | 97.12 | 97.89 | 1.41 |
| | | | | | | 230 | 9 | 83.35 | 98.11 | 0.77 |
| Example 5 | 33.5 | 30.7 | — | 5.9 | 2.3(Na) | 230 | 3 | 87.48 | 98.70 | 0.11 |
| | | | | | | 270 | 3 | 96.10 | 97.58 | 0.13 |

BDO = 1,4-butanediol, GBL = γ-butyrolactone, THF = tetrahydrofuran

EXAMPLE 6

A catalyst having the following composition was prepared as described in Example 3: 28.4% by weight of Cu, 25.0% by weight of Cr, 2.3% by weight of Mn, 1.6% by weight of Ba and 1.7% by weight of Na.

After reduction of the catalyst of an oxide form as described in Comparison Example 1, dehydrogenation of 1,4-butanediol was conducted in the following conditions in order to examine the life of the catalyst: reaction temperature of 232° C., pressure of 2 kg/cm$^2$G, weight hourly space velocity of 5 hr$^{-1}$ and molar ratio of H$_2$ to 1,4-butanediol of 6/1. The results are as shown in Table 2.

TABLE 2

| Reaction Time (hr) | Conversion of 1,4-butanediol (%) | Yield of γ-butyrolactone (%) |
| --- | --- | --- |
| 23 | 98.2 | 96.9 |
| 104 | 98.7 | 96.9 |
| 151 | 98.3 | 96.9 |
| 199 | 98.4 | 97.0 |
| 296 | 98.4 | 96.8 |
| 503 | 98.1 | 96.7 |
| 1006 | 98.3 | 96.7 |
| 1510 | 98.0 | 96.6 |
| 2015 | 97.1 | 95.8 |
| 2519 | 96.8 | 95.5 |
| 2855 | 96.7 | 95.4 |
| 3671 | 96.2 | 95.0 |
| 4223 | 96.0 | 94.8 |

EXAMPLE 7

Using the same catalyst as in Example 1, dehydrogenation of 1,4-butanediol was conducted in the following conditions: reaction temperature of 240° C., pressure of 4 kg/cm$^2$G, weight hourly space velocity of 3 hr$^{-1}$ and molar ratio of H$_2$ to 1,4-butanediol of 2/1. The results are as shown in Table 4.

Comparison Example 5

Using the same catalyst as in Comparison Example 1, dehydrogenation of 1,4-butanediol was conducted in the same conditions as in Example 7. The results are as shown in Table 4.

TABLE 4

| Reaction Time (hr) | Conversion of 1,4-butanediol (%) | | Yield of γ-butyrolactone (%) | |
| --- | --- | --- | --- | --- |
| | Ex. 7 | Comp. Ex. 5 | Ex. 7 | Comp. Ex. 5 |
| 50 | 98.3 | 99.7 | 96.3 | 96.7 |
| 100 | 98.2 | 99.8 | 96.2 | 96.8 |
| 150 | 98.4 | 99.7 | 96.3 | 96.6 |
| 200 | 98.2 | 99.5 | 96.3 | 96.5 |
| 300 | 98.1 | 99.6 | 96.1 | 96.5 |
| 400 | 98.0 | 99.3 | 96.0 | 96.1 |
| 500 | 97.8 | 98.8 | 95.9 | 95.6 |
| 750 | 97.6 | 98.0 | 95.6 | 94.9 |
| 1000 | 97.3 | 97.1 | 95.5 | 94.2 |
| 1500 | 96.7 | 93.5 | 94.9 | 89.0 |

EXAMPLE 8

(1) Preparation of a catalyst

To a solution of 150 g of $Na_2Cr_2O_7.2H_2O$ in 900 ml of distilled water were added 225 ml of an aqueous 28% ammonia, which is hereinafter referred to as Solution A.

In 900 ml of distilled water were dissolved 280 g of $Cu(NO_3)_2.3H_2O$, 26 g of $Mn(NO_3)_2.6H_2O$ and 8 g of $Ba(NO_3)_2$, and heated to 80° C. This solution is hereinafter referred to as Solution B.

Solution B was added to Solution A under stirring. The resultant precipitates were filtrated, washed with water, dried and pulverized, which was then pyrolyzed at 350° C. The powder obtained was washed with an aqueous 10% solution of acetic acid, washed with water and dried to obtain a catalyst precursor. To 100 g of the catalyst precursor were added 15 g of sodium silicate (water glass No. 1), dried and then calcined at 450° C. for 3 hours, to which graphite was added in an amount of 0.5% by weight. This was molded into pellets. The composition of the catalyst obtained in an oxide form which was determined in fluorescence X-ray analysis was as follows: 28.4% by weight of Cu, 25.0% by weight of Cr, 2.5% by weight of Mn, 1.6% by weight of Ba and 1.7% by weight of Na.

(2) Reduction of the catalyst

Ten ml of the catalyst in an oxide form were packed in a stainless steel (SUS 316) fixed bed reactor with a diameter of 15 mm and a length of 600 mm. The atmosphere in the system was sufficiently purged with a flow of nitrogen, which was then pressurized to 3 $kg/cm^2G$. A flow rate of nitrogen was 15 liters/hr (gas hourly space velocity of 1500 $hr^{-1}$).

Then, while maintaining the pressure and the gas flow rate, the nitrogen gas was replaced with nitrogen containing 0.1% by volume of hydrogen at room temperature and, subsequently, heating was started. The temperature was elevated at a rate of 30° C./hr up to 120° C.

After confirmed at 120° C. that the concentration of hydrogen at the gas outlet was identical to that at the gas inlet, the temperature was elevated to 130° C. over one hour. The temperature was then elevated from 130° C. to 140° C. over further one hour, from 140° C. to 150° C. over further one hour, and from 150° C. to 160° C. over further one hour, provided that the temperature was elevated after holding the predetermined temperature in each step until the concentration of hydrogen at the gas outlet became identical to that at the gas inlet.

Then, the concentration of hydrogen was increased gradually from 0.1% by volume to 0.3% by volume, and maintained for 2 hours.

The concentration of hydrogen was further increased gradually from 0.3% by volume to 0.5% by volume, and then the reduction temperature was elevated from 160° C. to 170° C. over one hour. When the temperature reached 170° C., the concentration of hydrogen was increased to 2.0% by volume and then held for one hour.

Subsequently, the concentration of hydrogen was increased stepwise, from 2.0% by volume to 5.0% by volume, 10.0% by volume and 100% by volume. In each step, the hydrogen concentration was held constant for 1 or 2 hours. When the concentration of hydrogen reached 100% by volume, the reduction temperature was elevated to 200° C. to end the reduction treatment. In each step, a next step was started after confirmed that the hydrogen concentration at the gas outlet was identical to that at the gas outlet.

Through the whole procedure of the reduction treatment in the above, temperature difference between the catalyst bed and the heating apparatus, $\Delta T$, due to heat generation of the catalyst bed did not exceed 5° C.

(3) Reaction

The catalyst obtained in the above step (2) was used in the following reaction.

The reactor was heated to 230° C. Then, 1,4-butanediol and hydrogen were passed in a ratio of 1 mole of 1,4-butanediol per 4 moles of hydrogen at an atmospheric pressure and a weight hourly space velocity of 1,4-butanediol of 5.0 $hr^{-1}$ to conduct dehydrogenation. The products were analyzed in gas chromatography to obtain the following results in mole percent:

| | |
|---|---|
| conversion of 1,4-butanediol | 94.4% |
| selectivity for γ-butyrolactone | 98.9%. |

Reference Example

This is to be compared with Example 8 in order to examine the influence of reduction procedure.

(1) Reduction treatment of a catalyst

Ten ml of the catalyst in an oxide form prepared in Example 8 were packed in a reactor as used in Example 8 and the atmosphere in the system was sufficiently purged with a flow of nitrogen, which was then pressurized to 3 $kg/cm^2G$. A flow rate of nitrogen was 15 liters/hr (gas hourly space velocity of 1500 $hr^{-1}$).

Then the catalyst layer was heated to 140° C. in an electric furnace and subsequently the nitrogen gas was replaced with nitrogen containing 3.0% by volume of hydrogen to start reduction. A total gas flow rate at that time corresponded to a gas hourly space velocity of 1500 $hr^{-1}$. After confirmed that heat generation due to reduction ended, the temperature was elevated gradually to 150° C. The temperature was further elevated to 170° C. at a rate of 10° C./hr further while confirming that the temperature of the catalyst bed was almost the same as that of the heating apparatus. After confirmed at 170° C. that heat generation ended, the concentration of hydrogen was increased to 10% by volume. The concentration of hydrogen was further increased to 100% by volume while holding the temperature at 170° C. When the concentration of hydrogen reached 100% by volume, the temperature was elevated to 200° C. to end the reduction of the catalyst.

The temperature difference, $\Delta T$, due to heat generation of the catalyst layer at a reduction temperature of 150° C. reached 12° C.

(2) Reaction

Using the catalyst reduced in above step (1), dehydrogenation of 1,4-butanediol was conducted in the same conditions as in Example 8. The results of gas chromatography for the products were as follows in mole percent:

| | |
|---|---|
| conversion of 1,4-butanediol | 89.0% |
| selectivity for γ-butyrolactone | 98.6%. |

Comparison Example 6

(1) Preparation of a catalyst

A catalyst containing only Cu and Cr was prepared in a similar manner as in Example 8. The composition of the catalyst in an oxide form was as follows: 36.2% by weight of Cu and 33.3% by weight of Cr.

(2) Reduction of the catalyst

The catalyst in an oxide form prepared in the above step (1) was reduced by the same method as in Example 8. The temperature difference, ΔT, due to heat generation by the reduction did not exceed 5° C. through the whole procedure.

(3) Reaction

Using the catalyst reduced in the above step (2), dehydrogenation of 1,4-butanediol was conducted in the same conditions as in Example 8. The results of gas chromatography for the products were as follows in mole percent:

| conversion of 1,4-butanediol | 85.7% |
|---|---|
| selectivity for γ-butyrolactone | 96.6%. |

EXAMPLES 9 to 12

The catalyst prepared in Example 8 was reduced as described in Example 8. Then, dehydrogenation of 1,4-butanediol was conducted as described in Example 8, except that reaction conditions were changed as indicated in Table 5. The results are as shown in Table 5.

TABLE 5

| | Ex. 9 | Ex. 10 | Ex. 11 | Ex. 12 |
|---|---|---|---|---|
| Reaction temp. (°C.) | 230 | 230 | 230 | 235 |
| Reaction pressure (kg/cm$^2$G) | 4.0 | 2.0 | 2.0 | 1.0 |
| Weight hourly space velocity (W.H.S.V.) (hr$^{-1}$) | 3.0 | 2.0 | 5.0 | 4.0 |
| H$_2$/BDO (molar ratio) | 4.0 | 6.0 | 6.0 | 5.0 |
| Conversion of BDO*$^1$ (%) | 97.8 | 99.5 | 96.8 | 98.2 |
| Selectivity for GBL*$^2$ (%) | 99.2 | 98.5 | 99.3 | 98.9 |

*$^1$BDO = 1,4-butanediol
*$^2$GBL = γ-butyrolactone

Temperature Programmed Desorption

A reason why the formation of by-products such as tetrahydrofuran was suppressed by the addition of the alkaline metals to the Cu-Cr catalyst is supposedly that acidic strength or acid amount of the catalyst was decreased by the alkali metals. In order to clarify this, acidic properties of the catalysts were determined in a TPD method with pyridine as follows. The catalysts used here were the Cu-Cr-Mn catalyst (a) prepared in Comparison Example 1, the Cu-Cr-Mn-Ba catalyst (a′) prepared in Comparison Example 2 and the Cu-Cr-Mn-Ba-Na catalyst (b′) prepared in Example 3.

Procedure of the determination: 0.3 g of the catalyst (30 to 100 mesh) was packed in a quartz tube. First, it was pre-treated by elevating the temperature to 100° C. at a rate of 20° C./min. in a flow of hydrogen. Then, the temperature was elevated to 250° C. at a rate of 5° C./min. and held for 2 hours to reduce the catalyst. Adsorption of pyridine to the catalyst was conducted in a flow of nitrogen at 200° C., and the temperature was maintained at 200° C. for several hours in a flow of nitrogen. The thermal desorption was conducted by elevating the temperature from 200° C. to 950° C. at a rate of 10° C./min. and pyridine desorbed was detected by a FID in gas chromatography.

Figure 2:
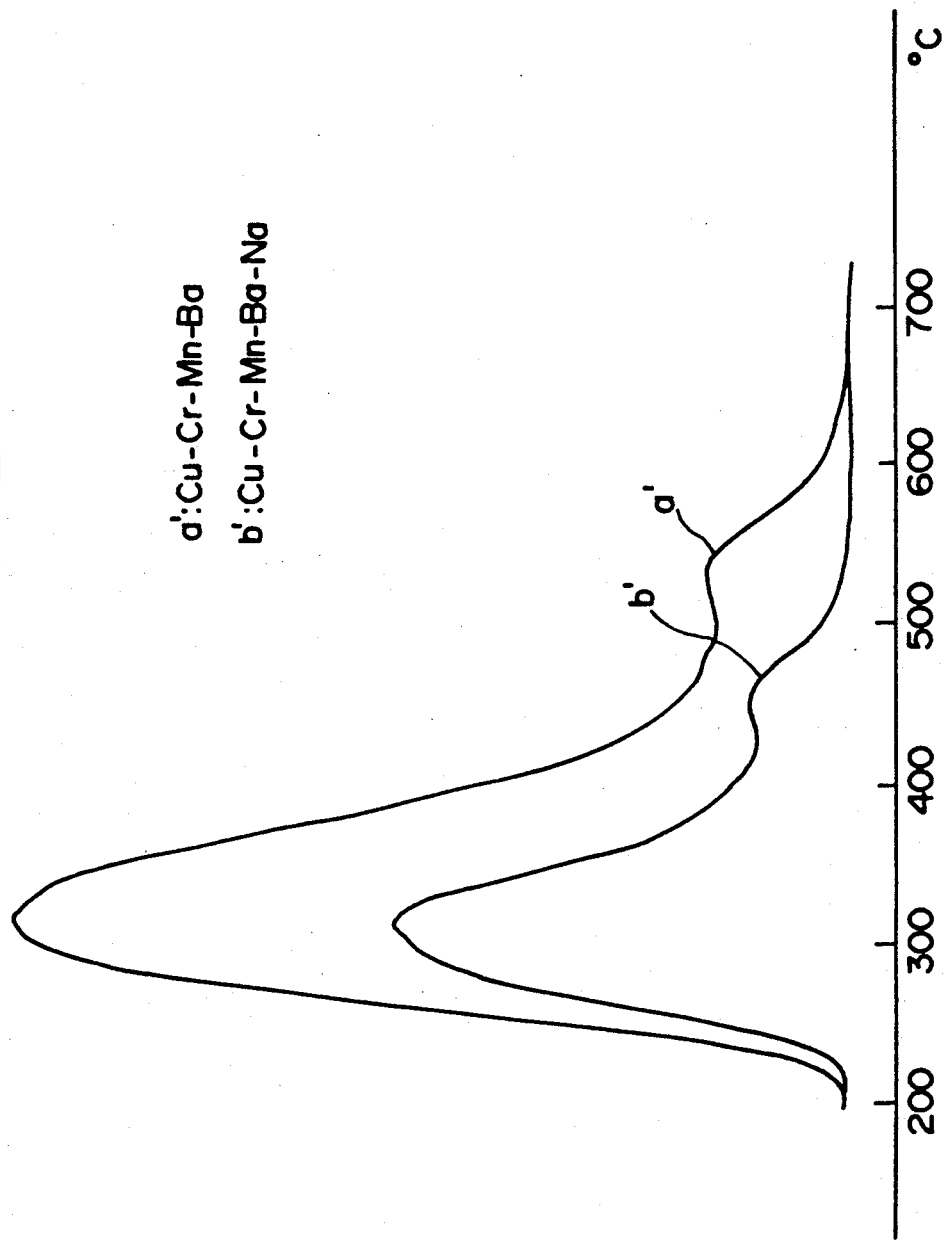
FIG. 2 also shows temperature programmed desorption profiles of pyridine on catalysts where curve (a') corresponds to the Cu-Cr-Mn-Ba catalyst prepared in Comparison Example 2, and curve (b') corresponds to the Cu-Cr-Mn-Ba-Na catalyst prepared in Example 3.

The results are as shown in FIGS. 1 and 2. The acid amounts in the catalysts (b) and (b′) which contained the alkali metals decreased, as a whole, compared to the Cu-Cr-Mn catalyst (a) and Cu-Cr-Mn-Ba catalyst (a′), respectively. Especially, it is seen that the peak in the higher temperature range between 500° and 600° C. disappeared almost and, thus, the acid strength was weakened by the addition of the alkali metal.

Thus, it has now been confirmed by TPD that the acidic properties of Cu-Cr type catalysts are changed by the addition of the alkali metal.

We claim:

1. A process for the preparation of γ-butyrolactone by catalytic dehydrogenation of 1,4-butanediol in a gaseous phase in the presence of a catalyst which contains copper, chromium, and at least one member selected from the group consisting of manganese and barium, characterized in that the catalyst further contains at least one member selected from the group consisting of sodium and potassium.

2. The process as claimed in claim 1, wherein the amount of sodium and potassium is 0.1 to 10 parts by weight as alkali metal per 100 parts by weight of the total of copper and chromium.

3. The process as claimed in claim 1, wherein the catalyst is subjected to reduction treatment in which the catalyst is heated from a temperature below 40° C. to a temperature of from 100° to 140° C. in a flow of an inert gas containing 0.1 to 1% by volume of hydrogen, and then the temperature and the hydrogen concentration are gradually raised.

4. The process as claimed in claim 2, wherein the catalyst is subjected to reduction treatment in which the catalyst is heated from a temperature below 40° C. to a temperature of from 100° to 140° C. in a flow of an inert gas containing 0.1 to 1% by volume of hydrogen, and then the temperature and the hydrogen concentration are gradually raised.

5. The process as claimed in claim 3, wherein an initial hydrogen concentration is in a range of from 0.1 to 0.5% by volume.

6. The process as claimed in claim 4, wherein an initial hydrogen concentration is in a range of from 0.1 to 0.5% by volume.

7. The process as claimed in any one of claims 1 or 3, wherein an atomic ratio of copper to chromium is 0.4 to 1.8.

8. The process as claimed in any one of claims 1 or 3, wherein the catalyst contains manganese in an amount of 1 to 10 parts by weight per 100 parts by weight of the total of copper and chromium.

9. The process as claimed in any one of claims 1 or 3, wherein the catalyst contains barium in an amount of 2 to 20 parts by weight per 100 parts by weight of the total of copper and chromium.

10. The process as claimed in any one of claims 1 or 3, wherein the catalyst contains both manganese and barium in a total amount of 3 to 30 parts by weight per 100 parts by weight of the total of copper and chromium.

11. The process as claimed in any one of claims 1 or 3, wherein the dehydrogenation is conducted at a reaction temperature of 150° to 300° C.

12. The process as claimed in any one of claims 1 or 3, wherein the dehydrogenation is conducted at reaction pressure of 0 to 8 kg/cm$^2$ in gauge pressure.

13. The process as claimed in any one of claims 1 or 3, wherein the dehydrogenation is conducted at a mole ratio of hydrogen to 1,4-butanediol of 0.5 to 10.

14. The process as claimed in any one of claims 1 or 3, wherein the dehydrogenation is conducted at a weight hourly space velocity of 1,4-butanediol of 0.2 to 16 hour$^{-1}$.

* * * * *